(12) United States Patent
Wynn et al.

(10) Patent No.: US 8,128,787 B2
(45) Date of Patent: Mar. 6, 2012

(54) MEMBRANE-AUGMENTED DISTILLATION WITH PRESSURE CHANGE TO SEPARATE SOLVENTS FROM WATER

(75) Inventors: Nicholas P. Wynn, Palo Alto, CA (US); Yu Huang, Palo Alto, CA (US); Masakatsu Urairi, Palo Alto, CA (US); Richard W Baker, Palo Alto, CA (US)

(73) Assignee: Nitto Denko Corporation, Osaka (JP)

( * ) Notice: Subject to any disclaimer, the term of this patent is extended or adjusted under 35 U.S.C. 154(b) by 195 days.

(21) Appl. No.: 12/229,790

(22) Filed: Aug. 27, 2008

(65) Prior Publication Data
US 2009/0004713 A1 Jan. 1, 2009

(51) Int. Cl.
  B01D 3/00 (2006.01)
  C07C 45/82 (2006.01)
  C07C 29/80 (2006.01)
  C07C 51/44 (2006.01)

(52) U.S. Cl. ........ 203/12; 203/15; 203/16; 203/17; 203/18; 203/19; 203/23; 203/24; 203/25; 203/26; 203/27; 203/75; 203/78; 203/DIG. 8; 203/DIG. 9; 203/DIG. 13; 210/640; 210/641; 435/162; 435/163; 568/916; 568/917

(58) Field of Classification Search ........ 203/3, 12, 203/15–19, 23–27, 39, 75, 78, DIG. 8, DIG. 9, 203/DIG. 13; 210/640, 641; 435/162, 163; 568/916, 917
See application file for complete search history.

(56) References Cited

U.S. PATENT DOCUMENTS

| | | | |
|---|---|---|---|
| 4,217,178 A * | 8/1980 | Katzen et al. | 203/19 |
| 4,294,664 A * | 10/1981 | Anthony | 203/19 |
| 4,340,446 A * | 7/1982 | Crawford | 203/19 |
| 4,372,822 A * | 2/1983 | Muller et al. | 203/19 |
| 4,405,409 A | 9/1983 | Tusel et al. | |
| 4,422,903 A * | 12/1983 | Messick et al. | 203/19 |
| 4,539,076 A | 9/1985 | Swain | |
| 4,978,430 A | 12/1990 | Nakagawa | |
| 5,035,776 A | 7/1991 | Knapp | |
| 5,105,029 A | 4/1992 | Ninomiya et al. | |
| 5,124,004 A * | 6/1992 | Grethlein et al. | 203/19 |
| 6,551,466 B1 * | 4/2003 | Kresnyak et al. | 203/1 |
| 7,297,236 B1 | 11/2007 | Vander Griend | |
| 7,744,727 B2 * | 6/2010 | Blum et al. | 203/19 |
| 2006/0070876 A1 | 4/2006 | Wu et al. | |
| 2007/0000769 A1 * | 1/2007 | Brown | 203/19 |
| 2008/0135396 A1 * | 6/2008 | Blum | 203/25 |
| 2009/0008235 A1 * | 1/2009 | Goel et al. | 203/41 |
| 2009/0057128 A1 * | 3/2009 | Vane et al. | 203/17 |
| 2009/0215139 A1 * | 8/2009 | Datta et al. | 435/162 |

* cited by examiner

Primary Examiner — Virginia Manoharan
(74) Attorney, Agent, or Firm — J. Farrant; K. Bean

(57) ABSTRACT

Processes for removing water from organic solvents, such as ethanol. The processes include distillation in two columns operated at sequentially higher pressure, followed by treatment of the overhead vapor by one or two membrane separation steps.

62 Claims, 9 Drawing Sheets

MEMBRANE-AUGMENTED DISTILLATION WITH PRESSURE CHANGE TO SEPARATE SOLVENTS FROM WATER

FIELD OF THE INVENTION

The invention relates to production and dehydration of solvents, especially alcohols. In particular, the invention relates to combinations of distillation and membrane separation to produce a dehydrated solvent product.

BACKGROUND OF THE INVENTION

The production of dry solvents from raw aqueous mixtures is often costly and complicated. The preparation of dry ethanol is a good example. In the conventional process, the raw fermentation broth is stripped under moderate vacuum in a beer still. Overhead vapor from the beer still is sent to a rectification column that produces an overhead product close to the azeotrope (about 93 wt % ethanol) and a bottoms product, which is essentially water. The condensed product from the top of the column is evaporated under pressure and fed to a molecular sieve dryer, which produces ethanol of 99 wt %+purity. Such a process consumes almost 100 million Btu/h to produce 50 million gallons per year of purified ethanol from a feed containing about 11 wt % ethanol.

It is known to use two distillation columns in series to separate mixtures such as organic/water mixtures. Such processes are taught in U.S. Pat. Nos. 4,539,076; 5,035,776; and 7,297,236, for example.

It is also known to use membrane separation to treat the overhead stream from a column. Such processes are taught in U.S. Pat. No. 4,978,430; in U.S. Published Application number 2006/0070867; in Japanese Published Application number JP7227517; and in U.S. patent application Ser. No. 11/896,201.

In addition, co-owned U.S. Pat. No. 7,732,173, issued Jun. 8, 2010, to Mairal et al., teaches a process for recovering ethanol involving membrane separation, followed by dephlegmation, followed by a second membrane separation step to dehydrate the overhead stream from the dephlegmator.

U.S. Pat. No. 5,105,029 teaches the use of two columns followed by membrane separation; and U.S. Pat. No. 4,405,409 discloses the use of two membrane separation steps in series to treat a column overhead.

Specific membranes for use in dehydration of organic compounds are taught in co-owned U.S. Pat. No. 8,002,874, issued Aug. 23, 2011, to Huang et al., and co-owned and copending U.S. application Ser. No. 11/897,675.

Despite the extensive efforts represented by the prior literature, there remains a need for a process that is both energy efficient and cost effective for producing high purity dehydrated solvents, especially ethanol.

SUMMARY OF THE INVENTION

The invention is a process for dehydrating solvents, particularly solvents that are readily miscible with water, and especially ethanol.

The process incorporates two distillation steps in series, operated at different pressures, followed by one or two membrane separation steps. The steps are integrated in such a way as to provide an operation that has both good energy efficiency and controlled capital costs.

In a basic embodiment, the process of the invention includes the following steps:

(a) subjecting at least a first portion of a solvent and water mixture to a first distillation step, carried out by passing a first feed stream of the mixture, at a first pressure, into a first column having a first reboiler system, to produce a solvent-enriched, first overhead vapor stream and a first bottoms stream;

(b) condensing the first overhead vapor stream to form a condensed overhead stream;

(c) pumping at least a portion of the condensed overhead stream to a second distillation step, carried out under a second pressure that is higher than the first pressure in a second column having a second reboiler system and a reflux condenser system, to produce a solvent-enriched, second overhead vapor stream and a second bottoms stream;

(d) performing a membrane separation step, comprising:
  (i) providing a membrane having a feed side and a permeate side, the membrane being selective in favor of water over solvent;
  (ii) passing at least a portion of the second overhead vapor stream at a feed pressure across the feed side;
  (iii) maintaining a permeate pressure on the permeate side that is lower than the feed pressure;
  (iv) withdrawing from the feed side, as a residue stream, a dehydrated product stream;
  (v) withdrawing from the permeate side a permeate stream enriched in water compared with the second overhead vapor stream;

(e) recovering heat by:
  (i) providing a heat exchanger that forms at least part of the first reboiler system;
  (ii) passing through the heat exchanger as a heating stream at least one stream selected from the group consisting of (I) the dehydrated product stream, (II) a reflux stream withdrawn from the second column, and (III) the second bottoms stream;
  (iii) passing a reboil stream withdrawn from the first column through the heat exchanger in heat exchanging relationship with the heating stream; and (f) recirculating the permeate stream within the process.

The first distillation step may be carried out solely as a stripping step driven by a reboiler at the base of the column. Alternatively, the column may include a reflux condenser, so that rectification also takes place in the column. The first distillation step is carried out at lower pressure than the second step, and optionally may be carried out at low temperatures and sub-atmospheric pressures, such as 0.5 bar or less.

The overhead vapor from the first column is condensed and pumped as liquid under pressure to the second distillation step.

The second distillation step may also be carried out solely as a stripping step driven by a reboiler at the base of the column, but more usually includes a rectification step also. The second distillation step is carried out at a higher pressure than the first step, and may be carried out at above atmospheric pressure, such as at 2 bar, 4 bar or higher.

Energy is recovered within the process by condensing the product stream, condensing the reflux for the second column, and/or cooling the bottoms stream from the second distillation step in a heat exchanger that serves as at least part of the reboiler system of the first column.

Further heating for the column may be provided by steam, for example.

The overhead from the second column is sent as feed to the membrane separation step. This step operates under a pressure difference between the feed and permeate sides of the membranes. The step divides the overhead stream into a residue stream, which is the dehydrated product of the process, and a permeate stream. To increase the driving force for transmembrane permeation, it is preferred to maintain the permeate side of the membranes under a partial vacuum. This also improves the pressure ratio for this step, which makes for a better separation between stream components.

The pressure ratio may be increased by using a vacuum pump in the permeate line to pull a vacuum on the permeate side. Optionally, the permeate stream is condensed, thereby creating the desired partial vacuum. The condensed stream is then circulated within the process, to the first or second distillation step in liquid form.

Alternatively, the permeate vapor may be returned as vapor to either column. In this case it is preferred to return the vapor to the first column, because this column is operating at a lower pressure than the second column.

The residue stream is withdrawn from the process, optionally after heat recovery as mentioned above.

More than one membrane separation step may optionally be used. Use of two membrane separation steps, with the residue from the first step forming the feed to the second, provides greater flexibility to tailor the process to control total energy usage. The permeate streams from each membrane separation step may be returned to different places in the process.

The raw solvent/water mixture to be treated may enter the process by passing into the first distillation step. It is also within the scope of the invention to split the raw feed, so that one portion is sent to the first column and another portion is sent to the second column. This type of embodiment can provide processes that combine low energy usage in such operations as the production of bioethanol.

It is also possible to use the process of the invention to treat two different feed mixtures simultaneously. For example, a plant processing both ethanol made from corn and ethanol made from cellulosic material can use the process of the invention in an energy-saving manner by sending the raw corn-based stream directly to the first column and the raw cellulose-based stream directly to the second column.

The processes of the invention can treat streams of any solvent/water composition, but are particularly suited to treating those in which the solvent is present at low concentrations, such as below 15 wt %, below 10 wt % or even below 5 wt %, such as only 1 wt % or 3 wt %. For the lowest solvent concentration feeds, designs with two membrane steps are especially beneficial.

In another aspect, the invention is a process for producing light alcohols, such as ethanol and isopropanol, by fermentation. The invention in this aspect includes the following steps:
(a) fermenting a sugar to form a fermentation broth comprising the alcohol and water;
(b) subjecting the fermentation broth to a first distillation step, carried out by passing a first feed stream of at least a first portion of the fermentation broth, at a first pressure, into a first column having a first reboiler system, to produce an alcohol-enriched, first overhead vapor stream and a first bottoms stream;
(c) condensing the first overhead vapor stream to form a condensed overhead stream;
(d) pumping at least a portion of the condensed overhead stream to a second distillation step, carried out under a second pressure that is higher than the first pressure in a second column having a second reboiler system and a reflux condenser system, to produce an alcohol-enriched, second overhead vapor stream and a second bottoms stream;
(e) performing a membrane separation step, comprising:
 (i) providing a membrane having a feed side and a permeate side, the membrane being selective in favor of water over alcohol;
 (ii) passing at least a portion of the second overhead vapor stream at a feed pressure across the feed side;
 (iii) maintaining a permeate pressure on the permeate side that is lower than the feed pressure;
 (iv) withdrawing from the feed side, as a residue stream, a dehydrated alcohol product;
 (v) withdrawing from the permeate side a permeate stream enriched in water compared with the second overhead vapor stream;
(f) recovering heat by:
 (i) providing a heat exchanger that forms at least part of the first reboiler system;
 (ii) passing through the heat exchanger as a heating stream at least one stream selected from the group consisting of (I) the dehydrated product stream, (II) a reflux stream withdrawn from the second column, and (III) the second bottoms stream;
 (iii) passing a reboil stream withdrawn from the first column through the heat exchanger in heat exchanging relationship with the heating stream; and
(g) recirculating the permeate stream within the process.

The fermentation step involves fermenting a sugar with any organism suitable for fermenting that sugar. The sugar may be from any source, including those formed by conversion of starchy, cellulosic and lignocellulosic materials.

In this process, it is possible to return the permeate stream, or one or both of the permeate streams if two membrane separation steps are used, to the fermentation step.

It is to be understood that the above summary and the following detailed description are intended to explain and illustrate the invention without restricting its scope.

DETAILED DESCRIPTION OF THE INVENTION

Figure 1:
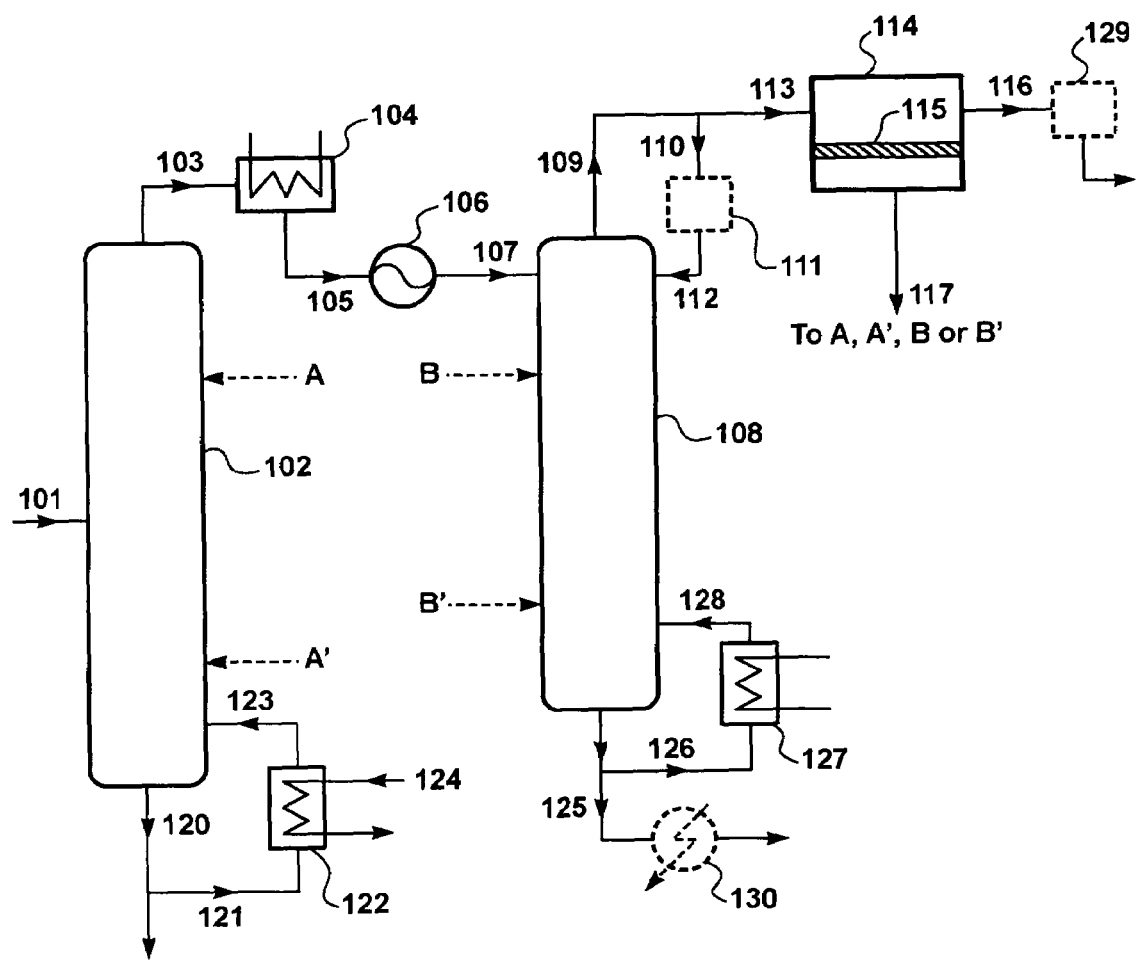
FIG. 1 is a schematic drawing showing the process flow scheme and apparatus elements for a basic embodiment of the invention.

The terms solvent/water solution and solvent/water mixture used herein refer to any mixtures or solutions of any organic compound and water that are generally liquid at room temperature and pressure, but that may be in the liquid or vapor phase during operation of the process.

The term selectivity as used herein refers to the selectivity of a membrane expressed as the ratio (water permeance)/(solvent permeance), as measured with membrane samples and with the solvent/water mixture of interest at the operating temperature at which the process is to be carried out.

The term rectification as used herein means composition adjustment of vapor by contact and interaction with condensed liquid.

The term stripping as used herein means composition adjustment of liquid by contact and interaction with evaporated vapor.

All liquid mixture percentages herein are by weight unless otherwise stated. Gas or vapor mixture percentages are by volume unless otherwise stated.

The invention is a process for dehydrating solvents, particularly solvents that are readily miscible with water, and especially ethanol.

The process of the invention can be used to separate essentially any solvent/water solution or mixture that can be distilled to produce a solvent-enriched overhead vapor stream. We believe the process of the invention is of particular value in separating solutions in which the organic component is in the range $C_1$-$C_6$, that is, has 1 to 6 carbon atoms, or where the solubility of water in the organic liquid at room temperature and pressure is at least about 5 wt %.

By way of example, the process of the invention is particularly useful for separating water from certain alcohols, ketones, aldehydes, organic acids and esters, including:
  ethanol, particularly bioethanol produced from natural sources ($C_2$)
  isopropanol ($C_3$)
  acetone ($C_3$)
  formaldehyde ($C_1$).

One or multiple organic compounds may be present in the mixture to be separated.

The feed stream may contain additional components besides organic solvents and water, such as inorganic salts, fermentation debris and the like. The feed stream may come from any source, and may be subjected to pretreatment, such as filtration, to remove contaminants before it enters the distillation column.

Representative sources of the feedstream include processes that manufacture organic solvents and processes that use organic solvents. Feedstreams that are particularly suited to treatment are those from the manufacture of light alcohols, ketones, aldehydes, organic acids and esters by chemical synthesis or fermentation.

Such manufacturing processes include, but are not limited to, chemical syntheses from petrochemical feedstocks, such as ethylene and propylene; fermentation of sugar-containing feedstocks; saccharification/fermentation of cellulosic and lignocellulosic feedstocks; and conversion of carbonaceous materials to syngas, followed by chemical or biochemical production of the desired solvent.

The solvent and water may be present in any ratio. The process is particularly useful and beneficial, however, in treating streams in which the initial solvent concentration is less than 50 wt %, such as less than 30 wt %, 20 wt %, 15 wt %, 10 wt %, 5 wt % or even less. Such streams are very hard to treat in an energy efficient and cost-effective manner by prior art processes.

In the discussion that follows, the representative operating parameters and preferences are given as they relate to the separation of ethanol/water mixtures in particular. Those of skill in the art will appreciate that preferences for stream compositions and so on may be different for other solvent/water mixtures, and will be able to adjust them based on the known physical properties of the solvent to be separated.

The process incorporates two distillation steps in series, operated at different pressures, followed by one or two membrane separation steps.

The invention in a basic embodiment is shown in FIG. 1. It will be appreciated by those of skill in the art that this figure, and the other figures are very simple schematic diagrams, intended to make clear the key aspects of the invention, and that an actual process train will usually include many additional components of a standard type, such as heaters, chillers, condensers, pumps, blowers, other types of separation and/or fractionation equipment, valves, switches, controllers, pressure-, temperature, level- and flow-measuring devices and the like.

In particular, the only sources of heat energy for the first column reboiler are shown as internal process streams. Additional heat energy from conventional sources, such as steam, will often be necessary to heat the reboil stream sufficiently, but these are familiar to those of skill in the art and have been omitted for clarity.

Also, the heat exchange is shown in FIG. 1 and the other figures as taking place in a unit external to the column, with a discrete reboil stream withdrawn to pass through the reboiler/heat exchanger. It will be apparent to those of skill in the art that a functionally equivalent result could be obtained if the heat donating streams flow in channels within the column itself.

Referring to FIG. 1, feed stream, 101, which is usually a liquid, is passed into first distillation column, 102. In the basic embodiment shown in FIG. 1, the first column takes the form of a stripping column, without a reflux condenser, although the column may optionally be equipped with a reflux system to provide rectification as well as stripping capability.

Energy for the stripping section is provided at least in part by reboiler heat exchanger, 122, in which a portion, 121, of the liquid bottoms stream, 120, is evaporated for return to the column as vapor stream, 123.

The column may be operated at any temperature and pressure appropriate to the separation that is to be carried out. For the separation of common organic solvents as listed above, operation at or below atmospheric pressure is commonly employed in prior art columns, and such operation is also preferred in our process. Thus representative preferred column pressures are in the range 0.05-1 bar, such as 0.5 bar or 0.1 bar, for example. In a non-limiting case, the column may be operated at 0.5 bar pressure with the overhead vapor being withdrawn at 70° C. or 80° C.

First overhead vapor stream, 103, exits the column. The composition of the overhead vapor is determined by the raw feed composition and the VLE under the operating conditions. A non-limiting typical guideline is to operate the column to produce an overhead vapor having a solvent concentration of about 5-10 times the feed solvent concentration if possible. In general, we prefer to operate the first column as a stripping column to deliver an overhead stream containing about 45-65 wt % solvent, such as about 55 or 60 wt % solvent.

The overhead stream is passed from the column to condenser or condensation step, 104. The resulting condensed overhead stream, 105, is pumped by liquid pump, 106, under pressure as stream, 107, to the second distillation column, 108, and enters the column, preferably at a tray position where the downcoming liquid matches its composition.

The second column is operated at any desired pressure that is higher than the pressure at which the first column is operated. Typically, it is preferred to operate the second column at above atmospheric pressure, such as at 2 bar, 3 bar, 4 bar, or 10 bar.

In the basic embodiment shown in FIG. 1, the second column is equipped with both a reboiler and a reflux condenser. Energy for the stripping section is provided at least in part by reboiler heat exchanger, 127, in which a portion, 126, of the second liquid bottoms stream, 125, is evaporated for return to the column as vapor stream, 128.

Bottoms stream, 125, is cooled before discharge in cooler, 130, which may optionally be a discrete unit, as indicated by the dashed symbol, or may form part of the reboiler system, 122, for the first column.

Reflux liquid for this column is preferably provided at least in part by reflux condenser, 111. The reflux condenser may optionally be a discrete unit, as indicated by the dashed box, or may form part of the reboiler system, 122, for the first column. In either case, a portion 110, of the second overhead vapor stream, 109, is condensed for return to the second column as reflux stream, 112.

Optionally, but less preferably, the reflux condenser may be omitted, so that the column has only stripping capability.

Preferably, the pressure and temperature operating conditions of the second column are set to deliver an overhead vapor stream with a solvent concentration of about 70-90 wt % solvent, more preferably about 75-85 wt % solvent, and most preferably at least about 80 wt % solvent.

If the raw feed to the process is very dilute, such as containing no more than about 5 wt % solvent, it is often convenient, and can result in lower overall energy usage, to operate the second column to achieve a lower overhead concentration, in the range 55-75 wt %, such as about 60 wt %, and to use two membrane separation steps, as explained below.

Overhead vapor that is not sent for reflux is passed as feed stream, 113, to membrane separation step or unit, 114, containing membranes, 115. A driving force for membrane permeation is provided by maintaining the permeate side of the membrane at a lower pressure than the feed side. Lowering the permeate pressure both increases the driving force for transmembrane permeation, increasing transmembrane flux, and increases the pressure ratio, improving the solvent/water separation performance.

The pressure difference and pressure ratio may be increased by using a vacuum pump in the permeate line to pull a vacuum on the permeate side. We have found, however, that simply cooling the permeate stream, 117, to condense the stream and create a spontaneous partial vacuum on the permeate side will provide an adequate pressure ratio in most separations. In this case, a pump may be needed only to remove any non-condensable gases, and to return the permeate stream to a destination within the process as discussed in more detail below.

Condensation of the permeate is achieved by cooling, typically by air or water cooling to lower the temperature to below 70° C., and preferably below 50° C. By operating in this manner, a pressure of 0.5 bar, 0.1 bar or lower can be reached on the permeate side.

As a typical example, the feed side may be at 3 bar total pressure and the permeate side at 0.5 bar or 0.25 bar pressure, providing a pressure ratio of 6 or 12.

The membranes, 115, may be of any type that provides selectivity in favor of water over the organic solvent. In any membrane separation, the enrichment in the permeate stream of the faster permeating component (by which we mean the concentration of that component in the permeate stream divided by the concentration in the feed) can never be greater than the pressure ratio (by which we mean the total pressure on the feed side divided by the total pressure on the permeate side), irrespective of the membrane selectivity.

The membrane separation step typically operates at a modest pressure ratio, such as less than 30, so a very high selectivity is not needed for this step. In general, the preferred membrane selectivity should be less than 100, and most preferably in the range of 10-100, such as up to about 20, 30, 50 or 60.

A selectivity higher than 100 can even be disadvantageous, as this implies a very low permeance for the slower permeating component, that is, the solvent. The membrane area requirements for the separation are controlled by the slower permeating component, so a very slow permeation rate for the solvent can lead to a very high membrane area requirement.

Subject to the above-preference for membranes of moderate selectivity, suitable membranes that can be used may be found within several classes, including polymeric membranes and inorganic membranes.

Representative water-selective membrane types include, but are not limited to, polymeric membranes having a hydrophilic selective layer, such as polyvinyl alcohol (PVA) or cellulose acetate, or having a hydrophobic selective layer of the type taught in U.S. pending application serial number 11/897,675, copending with the present application.

Yet other suitable membrane include chitosan membranes, and ion-exchange membranes, such as Nafion® membranes.

Inorganic membranes comprising hydrophilic materials may also be used as dehydration membranes. Such membranes include amorphous silica membranes and membranes including a water permeating zeolite layer, such as ZSM-5. Various types of inorganic membranes may be purchased from Mitsui and Company (USA) of New York, Isotronics of Paradise Valley, Ariz., Sulzer Chemtech Membrane Systems, based in Heinitz, Germany, and Pervatech BV of Enter, Netherlands.

The membrane separation unit can include a single membrane module or a bank or array of membrane modules.

Water permeates the membrane preferentially, to form water-enriched, solvent-depleted permeate stream, 117, in vapor form. This stream can be returned as vapor to either column, but preferably to the lower section of the first column. In this way, the latent heat content of the stream is recovered in the process.

Returning the permeate stream as a vapor reduces the energy consumption of the process and is particularly beneficial if the feed, 113, to the membrane separation step has a high water concentration, such as 25 wt % or above.

More normally, the water concentration is lower, such as 10-15 wt %. In this case the energy savings are less and it is preferred to condense the permeate stream as this increases the pressure ratio across the membrane, and reduces the amount of membrane area required to perform the separation.

The various position options within the scope of the invention for return of the permeate are indicated in FIG. 1 and other figures by dashed lines A, A' and B, B'. Wherever it is returned, recycle of the permeate stream within the process increases solvent recovery.

The residue stream, 116, from the membrane separation step is enriched in solvent compared with the feed stream, and is condensed in condensation step, 129, and withdrawn as the dehydrated product of the process.

Condensation step 129 may use a discrete condenser, as indicated by the dashed box, or may form part of the reboiler system, 122, for the first column.

As yet another alternative, the product stream may be condensed against the incoming feed stream.

The flow rate and composition of the residue stream depend on the operating features of the membrane separation step, such as pressure difference, pressure ratio, membrane selectivity and permeance, and membrane area. To achieve the preferred results, the membrane should typically provide a water permeance of at least about 1,000 gpu, and most preferably at least about 2,000 gpu, and a selectivity of at least 20, and preferably between 20 and 100, and the step should be operated at a pressure ratio of at least about 5 or 6.

The residue product stream preferably contains at least 90 wt % solvent, and more preferably at least 95 wt % solvent. Most preferably, the product is dehydrated to at least 98 wt % or 99 wt % solvent, or better.

If greater purity is needed than can conveniently be obtained using one membrane separation step, one or more additional membrane steps may be used to dehydrate the residue stream further. Alternatively, the residue stream can be passed to other non-membrane treatments.

The heat supply lines for the first reboiler are indicated for simplicity by single line, 124, in FIG. 1. As has been described above, however, heat energy is supplied from one, some or all of streams 110, 116 and 125. Additional energy to operate the reboiler and hence the first column is provided as needed by any other means, such as heat exchange against other process streams, or by steam heating, such as by direct steam injection into the column.

Figure 2:
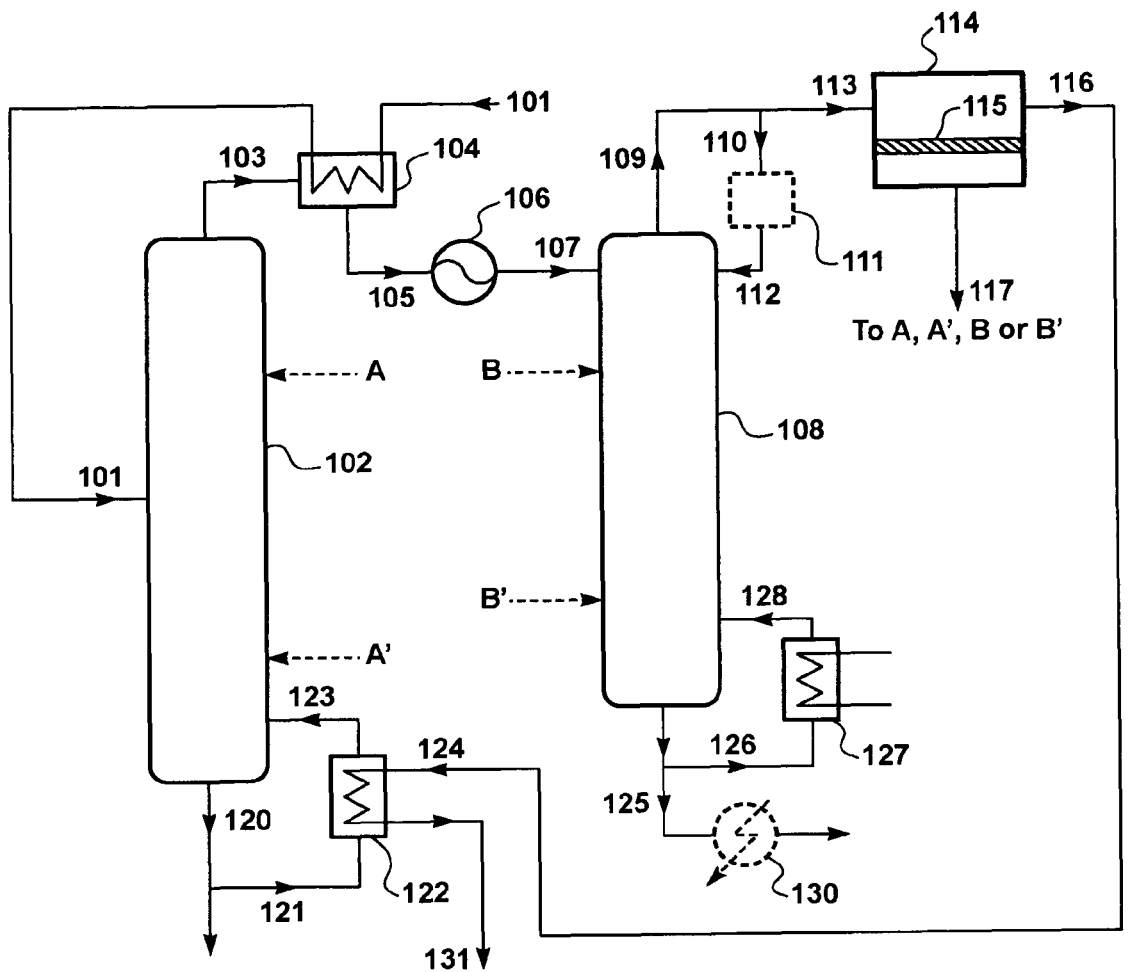
FIG. 2 is a schematic drawing showing a preferred embodiment of the invention in which the membrane residue product stream is condensed in the reboiler system of the first column, and the incoming feed is warmed by heat exchange in the overhead condenser between the columns.

FIG. 2 indicates a process configuration in which the membrane residue product stream is condensed in the reboiler system of the first column, and the incoming feed is warmed by heat exchange in the overhead condenser between the columns.

Like elements are numbered as in FIG. 1, and choices and preferences are similar to those for FIG. 1, except as explicitly stated otherwise.

In this case, stream 101 flows first through heat exchanger/condenser, 104, where it is warmed, typically to a temperature between about 35° C. and 75° C., such as 40° C., 50° C. or 60° C., and then enters the first column, 102.

Product residue stream, 116, is directed to line 124, and passes through reboiler/heat exchanger/condenser 122, where it condenses to form condensed product stream, 131.

Figure 3:
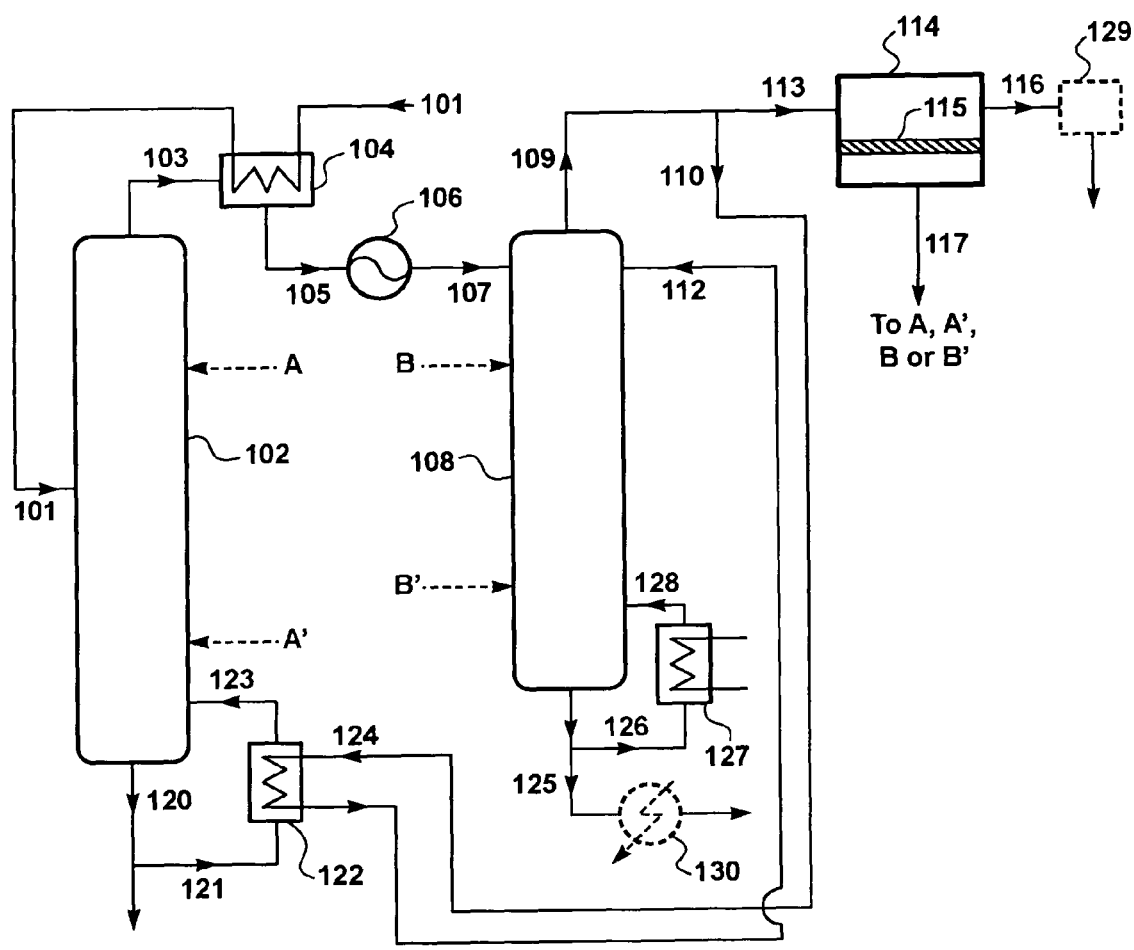
FIG. 3 is a schematic drawing showing an embodiment of the invention in which the reflux stream for the second column is condensed by heat exchange in the reboiler system of the first column, and the incoming feed is warmed by heat exchange in the overhead condenser between the columns.

FIG. 3 shows an embodiment of the invention similar to that of FIG. 2, except that the reflux stream for the second column is condensed by heat exchange in the reboiler system of the first column.

In this case, portion, 110, of the second overhead vapor stream, 109, is directed to line 124, and passes through reboiler/heat exchanger/condenser 122, where it condenses to form reflux stream, 112, for return to column 108.

Figure 4:
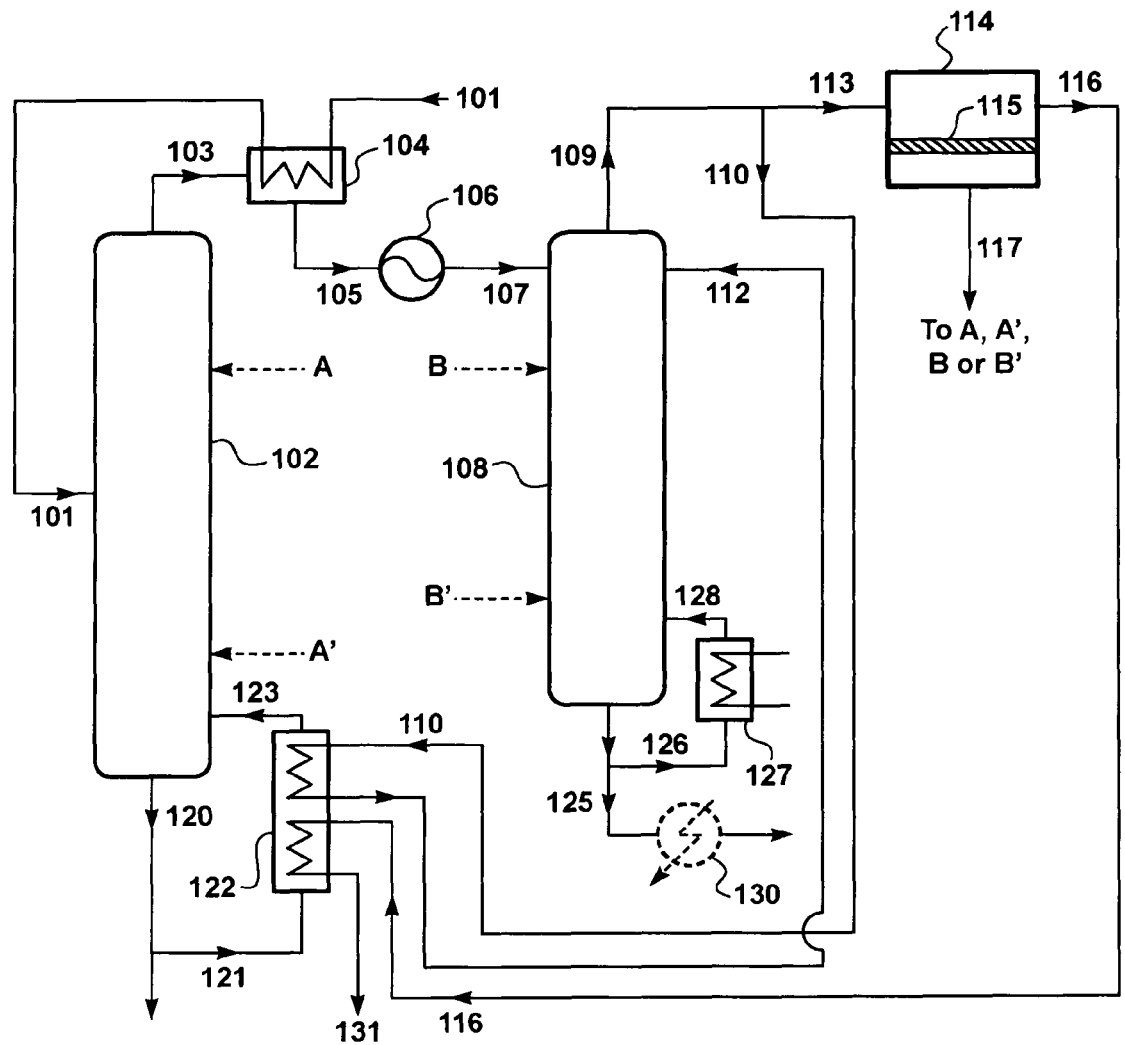
FIG. 4 is a schematic drawing showing a preferred embodiment of the invention in which the membrane residue stream and the reflux stream for the second column are condensed in the reboiler system of the first column, and the incoming feed is warmed by heat exchange in the overhead condenser between the columns.

A preferred embodiment of the invention similar to the embodiments of FIGS. 2 and 3, but in which both stream 116 and stream 110 are condensed in the first reboiler is shown in FIG. 4. As with FIG. 2, condensed product stream, 131, is withdrawn from the reboiler system and discharged from the process, and condensed reflux stream, 112, is returned to the second column.

In all of the designs illustrated so far and described above, only one membrane separation step is shown. However, in many instances, especially if the raw feed to be treated is relatively dilute, it can be advantageous to use two membrane separation steps in series to improve the purity of the product stream and reduce the overall amount of membrane area needed for the separation.

Figure 5:
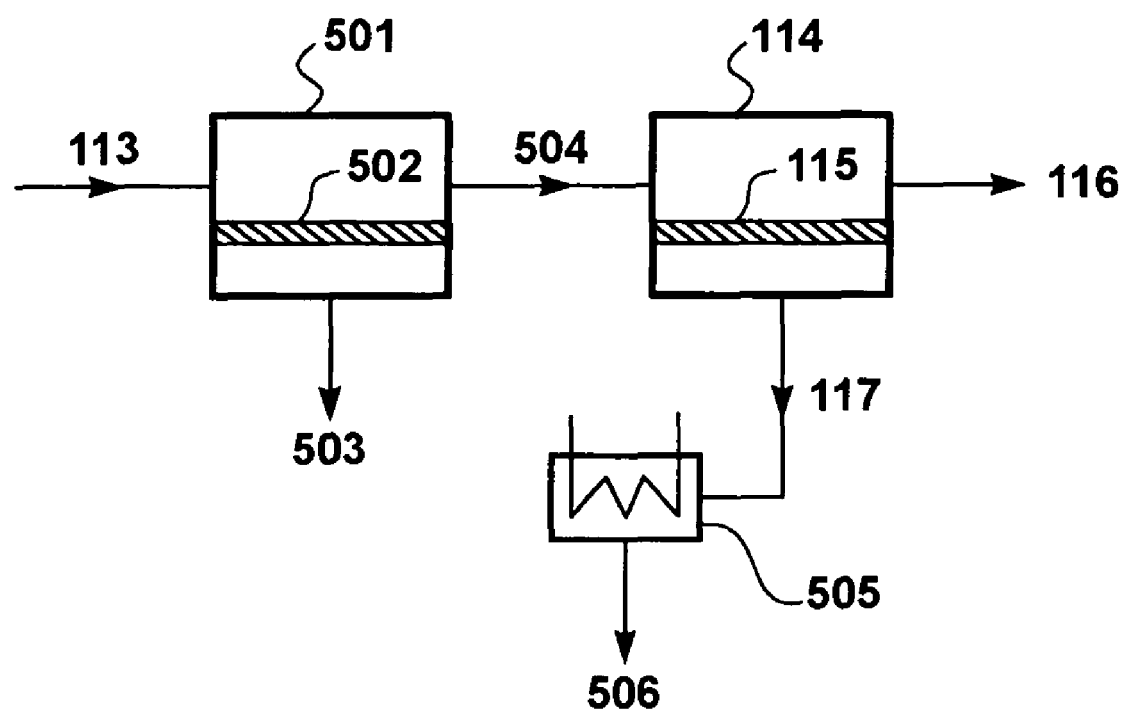
FIG. 5 is a schematic drawing showing the arrangement of two membrane steps in series as applied to the embodiments of FIGS. 1-4.

The application of two membrane separation steps as applied to any of the embodiments in the other figures is shown in FIG. 5. In this configuration, the additional membrane step is introduced upstream of step 114, which becomes the second membrane separation step.

Referring to FIG. 5, overhead vapor stream, 113, is passed to the additional, now the first, membrane separation step, 501, containing membranes, 502. The choices of membrane for this step are similar to those described above for the single membrane unit embodiments.

The first membrane unit separates stream 113 into a first permeate stream, 503, and a first residue stream, 504.

In this embodiment, the first membrane separation step acts as an intermediary separation between the second column and the second membrane step. As a result, the performance requirements for the first membrane step are less constrained than those for the second step, and the first step may operate at a lower pressure ratio than the second. In this case, a simple preferred option is to maintain the permeate side of the membrane at about the same pressure as the operating pressure of the first column, enabling the permeate stream to be returned to the column without adjusting the pressure. As a non-limiting option, a Roots blower or the like may be used to return the permeate as vapor to the column, in which case a small pressure differential may exist between the permeate side of the membranes and the column. For example, the permeate side may be at 0.25 bar and the column at 0.5 bar.

Alternatively, the permeate stream may be condensed in similar manner to that described above, and returned as liquid to the first or second column.

The first residue stream is passed as feed to the second membrane step or unit, 114, which corresponds to the single membrane unit or step of the previously described processes. Optionally, the membranes, 115, used in this step may be the same or different from those used in the first unit.

Likewise, the feed and permeate operating pressures and temperatures for the second membrane separation step may be the same or different from those for the first membrane separation step. In this design, the second membrane separation step delivers the treated product stream, so it is preferred to operate this step with a deeper vacuum on the permeate side if possible to increase pressure ratio.

If the second membrane separation step is operated at a higher pressure ratio than the first membrane separation step, this step is less pressure ratio limited than the first step. A higher selectivity may then be beneficial, and preferred membranes for the second step have selectivities up to 200 or 250.

As with the other embodiments, a vacuum pump may be used in the second permeate line, 117, to pull a vacuum on the permeate side, although in most cases it is simpler, and preferred, to lower the permeate pressure to the desired value by condensing, 505, at an appropriate temperature. The condensed permeate stream, 506, is returned within the process, preferably to the second column.

The residue stream, 116, from the second membrane step is the dehydrated product stream, and is condensed and discharged as described above.

In the designs described above, all of the raw feed stream enters the process at the first distillation column. It is also within the scope of the invention to split the raw feed, so that one portion is sent to the first column and another portion is sent to the second column. This type of embodiment can provide processes with very low total energy usage for the purification of bioethanol for example.

It is also possible to use the process of the invention to treat two different feed mixtures simultaneously. Such an embodiment can be useful, for example, if two feeds from different sources, or having different concentrations of solvent, are to be treated.

Figure 6:
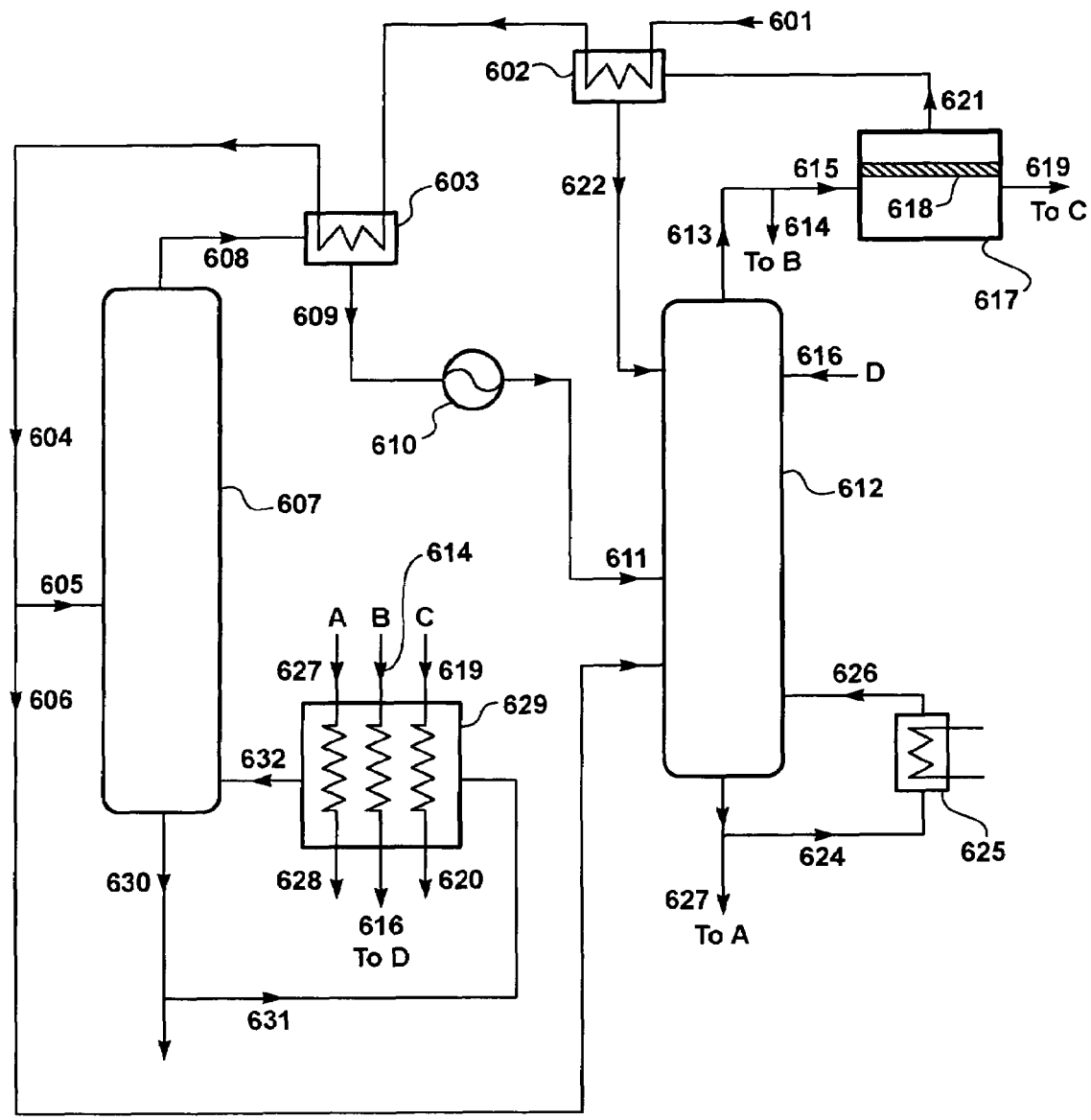
FIG. 6 is a schematic drawing showing a specific preferred embodiment of the invention, with heat exchange between the reboil stream for column one and the membrane residue product stream, reflux stream for column two, and bottoms stream from column two; and in which the incoming feed is warmed by heat exchange in the permeate condenser and the condenser for the first column overhead, then split, with a portion being send as raw feed to each column.

FIG. 6 illustrates a particularly preferred embodiment of the invention to treat a single split feed, using heat recovery from multiple streams. As before, options and preferences are the same as for FIG. 1, unless stated to be otherwise.

Referring to FIG. 6, raw feed stream, 601, enters the process and is warmed by heat exchange against permeate stream, 621, in heat exchanger/condenser, 602, and against first overhead vapor stream, 608, in heat exchanger/condenser, 603.

Warmed feed, 604, is split into two portions, 605 and 606. In general, at least 50% of the feed is directed to stream 605, and it is preferred to split the feed so as to send between about 65-85% of the feed to the first column, as we have discovered that this range offers the best overall energy efficiency for the process. Most preferably, 70-80% of the feed is directed to stream 605, and the remaining 30-20% to stream 606.

Stream 605 passes into first distillation column, 607. Energy for operating this column is provided at least in part by first reboiler/heat exchanger system, 629, in which a portion, 631, of the liquid bottoms stream, 630, is evaporated for return to the column as heated vapor stream, 632.

In this case, three streams from within the process supply heat to the reboiler system: stream 627, the bottoms stream from the second column, which is passed into the heat exchanger as shown at A; stream 614, the reflux stream for the second column, which is passed into the heat exchanger as shown at B; and stream 619, the residue product stream, which is passed into the heat exchanger as shown at C. As always, additional heat energy may be supplied by steam or any other source.

First overhead vapor stream, 608, is passed from the column to condensation step or condenser, 603, and the condensate stream, 609, is pumped by liquid pump, 610, under pressure as liquid, 611, to the second distillation column, 612. If stream 608 is too large to be completely condensed by stream 601, an additional cooling stream, such as cooling water, may be used to complete the condensation. The condensate, 609, preferably enters the column at a tray position where the downcoming liquid matches its composition. The second portion, 606, of the raw feed also enters the second column.

Condensed reflux liquid for this column, stream 616, returns from the reboiler system as shown at D.

The column has a reboiler system, 625, through which a portion, 624, of bottoms stream, 625, is passed for return as hot vapor reboil stream, 626.

The bottoms, 627, from the column are passed to reboiler system 629 for heat recovery, as described above, and are discharged from the process as cooled stream, 628.

The portion, 615, of second overhead vapor stream, 613, that is not sent for reflux is passed as a feed stream to membrane separation step, 617, which uses membranes, 618. Product residue stream, 619, is withdrawn from the membrane separation step, condensed in reboiler system 629, and discharged from the process as liquid product stream, 620.

The permeate stream, 621, is condensed against the incoming feed and returned to the second column as stream, 622.

Figure 7:
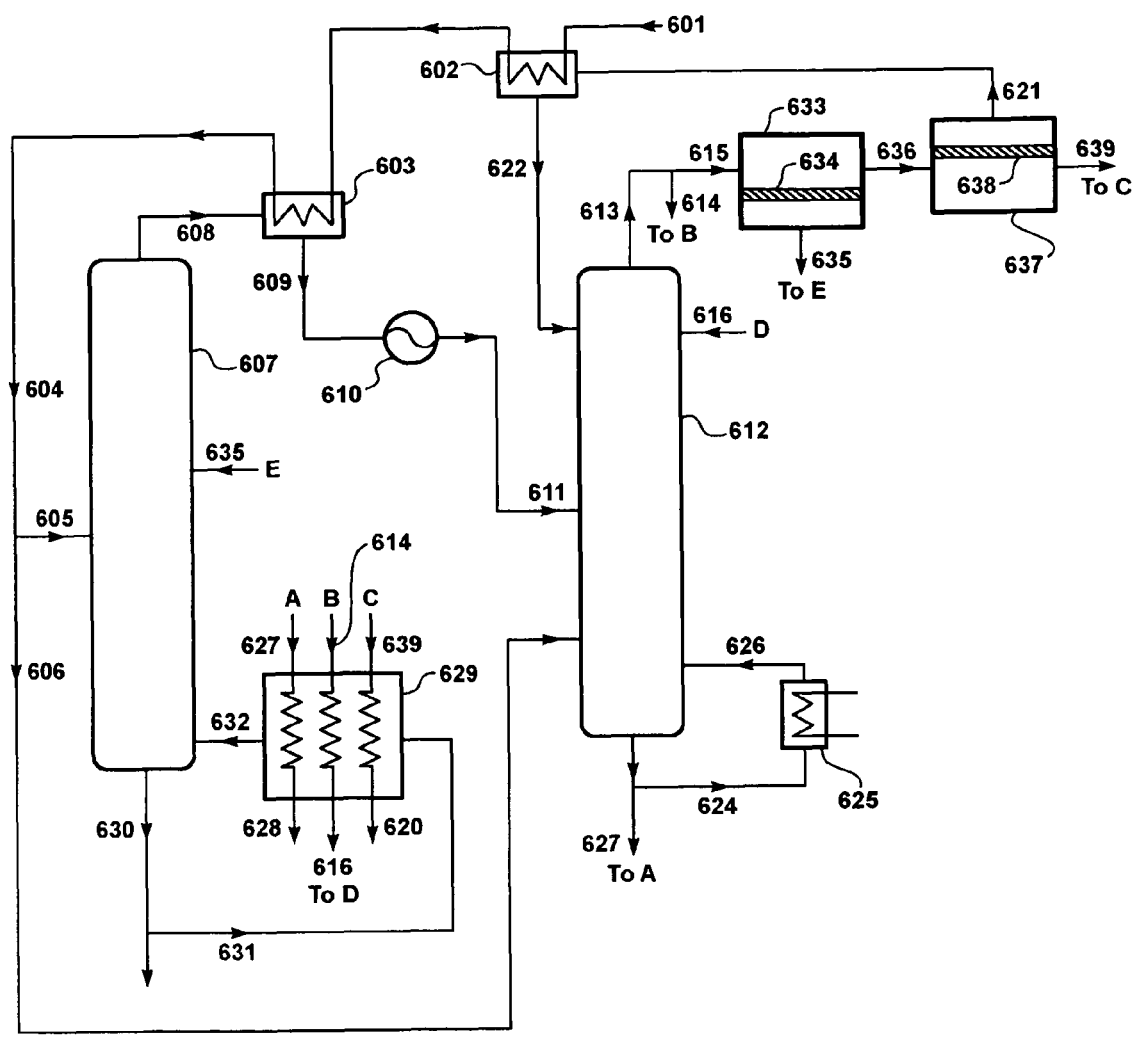
FIG. 7 is a schematic drawing of a process similar to that of FIG. 6, except that two membrane separation steps are used.

FIG. 6 shows an embodiment using one membrane separation step; a similar embodiment, but using two membrane separation steps, is shown in FIG. 7, in which like elements are numbered as in FIG. 6.

Referring to FIG. 7, overhead stream 615 now passes to a first membrane separation step, 633, using membranes, 634, to separate the stream into residue stream, 636, and permeate stream, 635.

The permeate stream is returned as vapor to the first column, as shown at E. The residue stream passes as feed to the second membrane separation step, 637, using membranes, 638. The permeate from this step passes as stream 621 to condenser 602, as in FIG. 6. The second residue stream, 639, is the product of the process, and is condensed in reboiler system 629 to form liquid product stream, 620.

Both FIG. 6 and FIG. 7 show a process in which a single feed, 601, is split. As mentioned above, however, similar processes may be used to treat feeds from different sources, with one feed entering as stream 605 and the other as stream 606. Either or both streams may be directed through heat exchanger 602 and/or heat exchanger 603 before entering the distillation columns.

As one example, one feed may be from the fermentation of corn to ethanol, and may contain proteins and other biological matter in addition to ethanol and water. If this feed were to be sent directly to the high-pressure column, these materials could deposit out as solids in the column, fouling the trays and impairing column performance. In this case, this feed cannot be split (unless previously treated to remove the contaminants), and is sent entirely to the first column.

If the plant also processes cellulosic materials, such as corn stover, however, the raw fermentation product from the cellulosic feed is relatively free of proteins and fats, although it may typically contain only about 5 wt % ethanol. This product can be sent as the second feed directly to the high-pressure column.

In another aspect, the invention is a process for producing light alcohols by fermentation, using a combination of steps including fermentation, distillation at two different pressures, and membrane separation. The invention in this is illustrated in FIG. 8, where, once again options and preferences are the same as for FIG. 1, unless stated otherwise.

Figure 8:
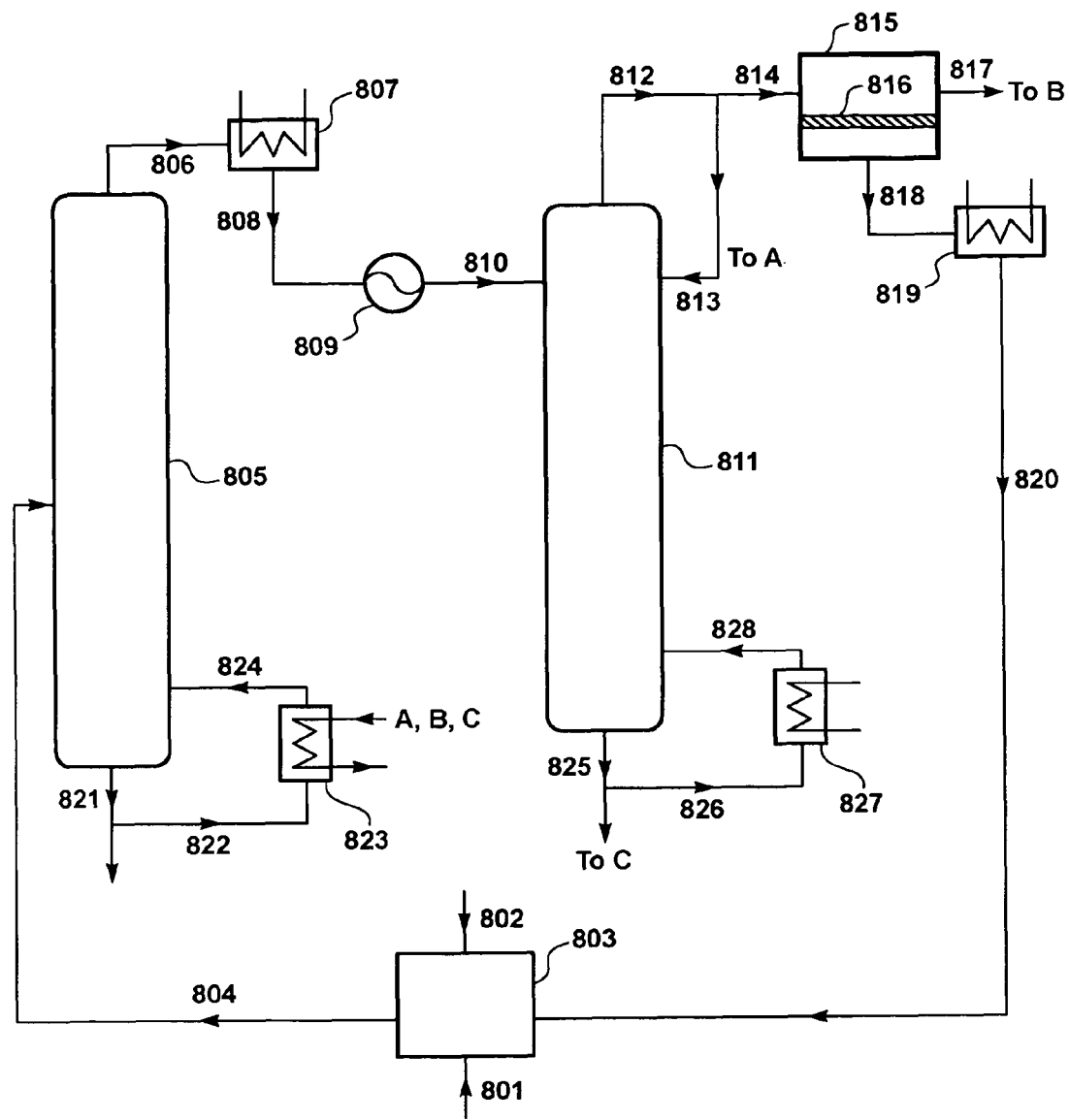
FIG. 8 is a schematic drawing of a process of the invention in an aspect that relates to the production of a light alcohol using a single membrane separation step.

Referring to FIG. 8, a feedstock, 801, and a fermentation agent, 802, enter fermentation step or vessel, 803. The feedstock may be any material that contains a fermentable sugar.

Preferred sources of feedstock include waste materials that contain sugar, starch, cellulosic or other substances that can be converted to sugar. These types of waste are diverse, and include: food-processing wastes, such as cheese whey; other agricultural wastes, such as grape skins; and cellulosic wastes, such as corn stover or wood waste. Other examples of feedstocks include biomass that may be grown specifically as a source of raw material for alcohol production, such as cereal grains, grasses, sugarcane and root crops.

The fermentation step may be carried out using any reaction that can convert a sugar to an alcohol. Preferably the reaction is the commonplace enzymatic reaction using yeast to ferment a six-carbon sugar to ethanol. Other representative fermentation reactions include the use of clostridium organisms. The step may be carried out in any type of batch or continuous mode.

If the source material itself does not contain adequate quantities of sugar, but may be treated to form sugars, the invention may include one or more additional steps to carry out appropriate treatment, such as to convert starch or cellulose to sugar, or to break down lignin and then convert exposed cellulose. These steps may be carried out as pretreatment before the material enters the fermentation vessel, or may be performed simultaneously with the fermentation step.

The invention may include one or more filtration steps between the fermentation step and the first membrane separation step, to recover yeast cells, to remove other suspended solid matter that might foul the membranes in the membrane separation step, to remove dissolved nutrients, salts or excess sugar, or otherwise to prepare the feed to the membrane separation step. Depending on the materials to be removed, this filtration step can optionally include one or more of microfiltration, ultrafiltration, nanofiltration or reverse osmosis.

Stream, 804, containing light alcohol and water, is passed from the fermentation step or unit to first distillation step or column, 805. Energy for operating the first column is provided at least in part by reboiler/heat exchanger system, 823, in which a portion, 822, of the liquid bottoms stream, 821, is evaporated for return to the column as heated vapor stream, 824.

First overhead vapor stream, 806, is passed from the column to condenser or condensation step, 807, and the resulting condensed stream, 808, is pumped, 809, to the second column, 811, as pressurized liquid stream, 810.

The second column is equipped with a reboiler, 827, in which a portion, 826, of the liquid bottoms stream, 825, is evaporated for return to the column as heated vapor stream, 828.

A portion, 813, of the second overhead vapor stream, 812, is condensed in reboiler 823, as indicated by the letter A, and returned to the second column as reflux.

Overhead vapor that is not sent for reflux is passed as feed stream, 814, to membrane separation step or unit, 815, containing membranes 816. Dehydrated alcohol product residue stream, 817, is withdrawn from the membrane separation steps, and may be condensed in heat exchanger 823 as indicated by the letter B, or elsewhere within the process as desired for additional heat recovery.

In this case, the permeate stream, 818, from the membrane separation step is condensed, 818, and recirculated to the fermenter as stream, 820.

Figure 9:
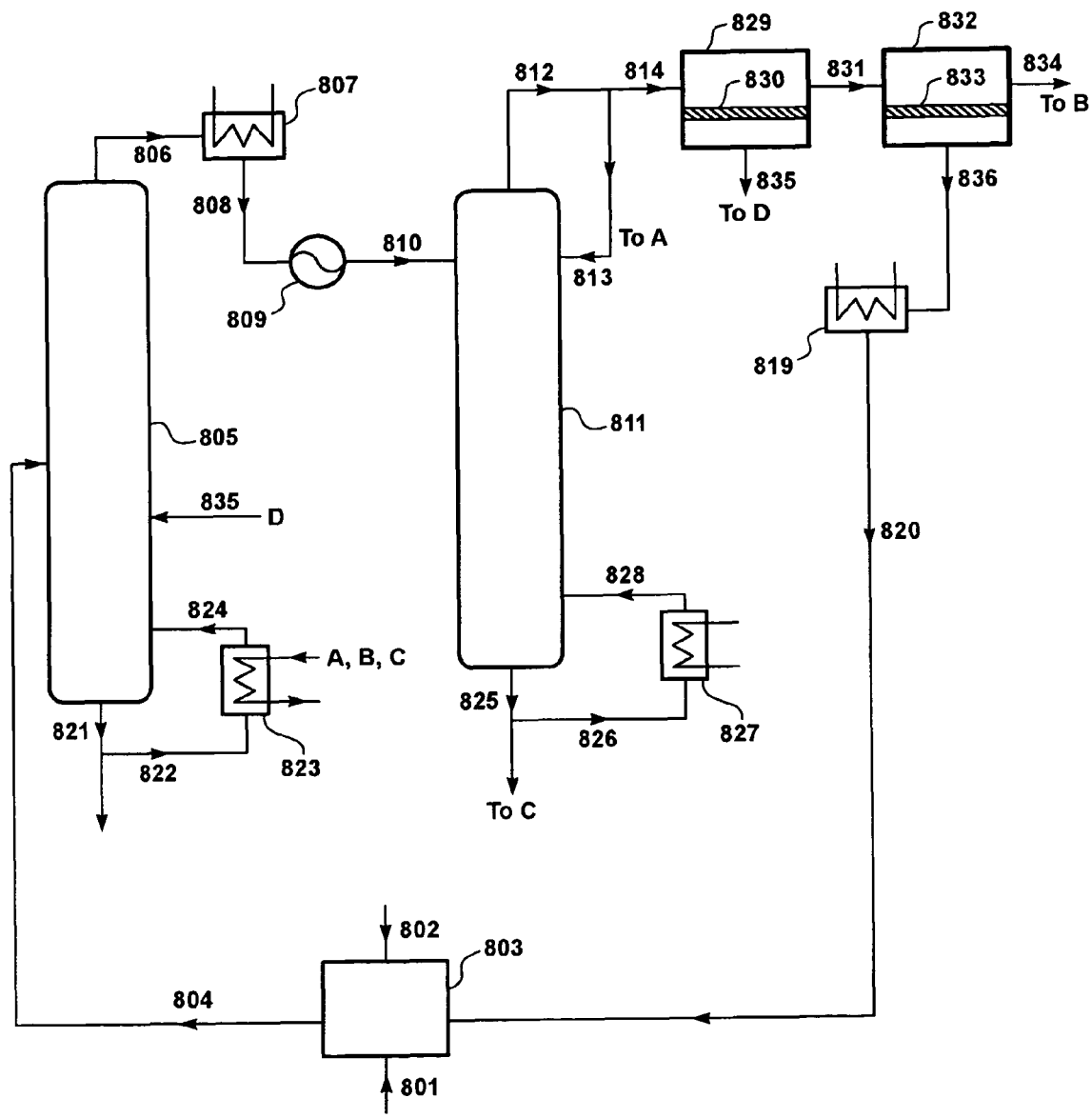
FIG. 9 is a schematic drawing of a process of the invention in an aspect that relates to the production of a light alcohol using two membrane separation steps.

FIG. 8 shows an embodiment of an alcohol-making process using one membrane separation step; a similar embodiment, but using two membrane separation steps, is shown in FIG. 9, in which like elements are numbered as in FIG. 8.

Referring to FIG. 9, overhead stream 814 now passes to a first membrane separation step, 829, using membranes, 830, to separate the stream into residue stream, 831, and permeate stream, 835.

The permeate stream is returned as vapor to the first column, as shown at D. The residue stream passes as feed to the second membrane separation step, 832, using membranes, 833. The permeate, 836, from this step passes to condenser 819, as in FIG. 8, and returns to the fermenter. The second residue stream, 834, is the product of the process, and is condensed in reboiler system 823.

The invention is now further described by the following examples, which are intended to be illustrative of the invention, but are not intended to limit the scope or underlying principles in any way.

EXAMPLES

Example 1

A computer calculation was performed with a modeling program, ChemCad 5.5.1 (ChemStations, Inc., Houston, Tex.) to illustrate the process of the invention in the embodiment shown in FIG. 6.

The calculation assumed that the feed composition was 11.5% ethanol and 88.5% water, representative of a raw feed from a bioethanol manufacturing process. The raw feed was assumed to be split 70%/30% between the first and second columns.

The process was assumed to use a stripping column, having 15 stripping stages and a stripping/rectification column, having 15 stages also. The columns were assumed to operate at 0.5 bar and 3 bar respectively.

The process was configured to provide a rectified overhead stream, 615, containing about 80 wt% ethanol, and a dehydrated product stream, 619, containing 99.7 wt % ethanol. The membranes were assumed to have a selectivity for water over ethanol of about 30, consistent with the membranes described in co-owned U.S. Pat. No. 8,002,874, issued Aug. 23, 2011, to Huang et al., and co-owned and copending U.S. application Ser. No. 11/897,675, for example. The results of the calculations are summarized in Table 1.

TABLE 1

| | Stream | | | | | | |
|---|---|---|---|---|---|---|---|
| | 601 (Feed) | 611 | 615 (Rectified overhead) | 621 | 627 | 630 | 619 (Product ethanol) |
| Flow (kg/h) | 165,000 | 22,117 | 47,985 | 29,097 | 52,729 | 93,383 | 18,888 |
| Temp (° C.) | 37 | 62 | 117 | 113 | 91 | 81 | 91 |
| Pressure (bar) | 1.0 | 3.0 | 3.0 | 0.5 | 3.0 | 0.5 | 3.0 |
| Component | | | | | | | |
| Water | 88.5 | 40.4 | 20.0 | 32.8 | 99.9 | 99.9 | 0.3 |
| Ethanol | 11.5 | 59.6 | 80.0 | 67.2 | 0.1 | 0.1 | 99.7 |

The process was calculated to use total energy of 52.8 million Btu/h, and 21,000 m² of membrane area.

Example 2

The calculation of Example 1 was repeated, but this time assuming that two membrane separation steps were used, as in FIG. 7, with the permeate from the first step being returned as vapor to the first column. The results of the calculations are summarized in Table 2.

TABLE 2

| | Stream | | | | | | |
|---|---|---|---|---|---|---|---|
| | 601 (Feed) | 611 | 615 (Rectified overhead) | 621 | 635 | 627 | 630 | 639 (Product ethanol) |
| Flow (kg/h) | 165,000 | 24,864 | 30,363 | 6,550 | 4,925 | 50,561 | 95,560 | 18,888 |
| Temp (° C.) | 37 | 62 | 117 | 114 | 117 | 91 | 81 | 91 |
| Pressure (bar) | 1.0 | 3.0 | 3.0 | 0.1 | 0.5 | 3.0 | 0.5 | 3.0 |
| | Component | | | | | | |
| Water | 88.5 | 41.4 | 20.0 | 37.7 | 72.0 | 99.9 | 99.9 | 0.3 |
| Ethanol | 11.5 | 58.6 | 80.0 | 62.3 | 28.0 | 0.1 | 0.1 | 99.7 |

The process was calculated to use total energy of 59.6 million Btu/h, and 5,570 m² of membrane area.

Comparing Examples 1 and 2, it may be seen that both are able to produce a high-quality product containing 99.7 wt % ethanol. In situations where controlling energy usage is of paramount importance, the first process is preferred because of the lower energy usage. If energy constraints are not so severe, the second process, which uses slightly more energy, but much less membrane area, is preferred, because the overall system is simpler and much more compact.

Example 3

The calculation of Example 1 was repeated, but this time assuming that the feed to the process contained only 3 wt % ethanol.

The results of the calculations are summarized in Table 3.

TABLE 3

| | Stream | | | | | | |
|---|---|---|---|---|---|---|---|
| | 601 (Feed) | 611 | 615 (Rectified overhead) | 621 | 627 | 630 | 619 (Product ethanol) |
| Flow (kg/h) | 645,000 | 43,879 | 46,192 | 27,410 | 218,596 | 407,621 | 18,783 |
| Temp (° C.) | 37 | 65 | 117 | 113 | 91 | 81 | 91 |
| Pressure (bar) | 1.0 | 3.0 | 3.0 | 0.5 | 3.0 | 0.5 | 3.0 |
| | Component | | | | | | |
| Water | 97.0 | 70.1 | 18.0 | 30.1 | 99.9 | 99.9 | 0.3 |
| Ethanol | 3.0 | 29.9 | 82.0 | 69.9 | 0.1 | 0.1 | 99.7 |

The process was calculated to use total energy of 146.3 million Btu/h, and 20,500 m² of membrane area.

Example 4

The calculation of Example 2 was repeated, but this time assuming that the feed to the process contained only 3 wt % ethanol.

The results of the calculations are summarized in Table 4.

TABLE 4

| | \multicolumn{8}{c}{Stream} | | | | | | | |
|---|---|---|---|---|---|---|---|---|
| | 601 (Feed) | 611 | 615 (Rectified overhead) | 621 | 635 | 627 | 630 | 639 (Product ethanol) |
| Flow (kg/h) | 645,000 | 48,778 | 30,193 | 6,514 | 4,897 | 218,607 | 407,619 | 18,788 |
| Temp (° C.) | 37 | 65 | 117 | 114 | 117 | 91 | 81 | 91 |
| Pressure (bar) | 1.0 | 3.0 | 3.0 | 0.1 | 0.5 | 3.0 | 0.5 | 3.0 |
| | | | | Component | | | | |
| Water | 97.0 | 70.3 | 20.0 | 37.7 | 72.0 | 99.9 | 99.9 | 0.3 |
| Ethanol | 3.0 | 29.7 | 80.0 | 62.3 | 28.0 | 0.1 | 0.1 | 99.7 |

The process was calculated to use total energy of 141.5 million Btu/h, and 5,536 m$^2$ of membrane area.

Comparing Examples 1 and 2, it may be seen that both are able to produce a high-quality product containing 99.7 wt % ethanol. In situations where controlling energy usage is of paramount importance, the first process is preferred; where slightly higher energy usage can be tolerated, the second process can be carried out with many fewer membrane modules, making for a more compact system.

Comparing Examples 3 and 4, it may be seen that both are able to produce a high-quality product containing 99.7 wt % ethanol. The process using two membrane separation steps uses about a quarter of the membrane area needed for the process with a single membrane step.

We claim:

1. A process for recovering an organic solvent from a solvent and water mixture, comprising:
   (a) subjecting at least a first portion of the mixture to a first distillation step, carried out by passing a first feed stream of the mixture, at a first pressure, into a first column having a first reboiler system, to produce a solvent-enriched, first overhead vapor stream and a first bottoms stream, wherein the first bottoms stream consists essentially of water;
   (b) condensing the first overhead vapor stream to form a condensed overhead stream;
   (c) pumping at least a portion of the condensed overhead stream to a second distillation step, carried out under a second pressure that is higher than the first pressure in a second column having a second reboiler system and a reflux condenser system, to produce a solvent-enriched, second overhead vapor stream and a second bottoms stream;
   (d) performing a membrane separation step, comprising:
      (i) providing a membrane having a feed side and a permeate side, the membrane being selective in favor of water over solvent;
      (ii) passing at least a portion of the second overhead vapor stream at a feed pressure across the feed side;
      (iii) maintaining a permeate pressure on the permeate side that is lower than the feed pressure;
      (iv) withdrawing from the feed side, as a residue stream, a dehydrated product stream;
      (v) withdrawing from the permeate side a permeate stream enriched in water compared with the second overhead vapor stream;
   (e) recovering heat by:
      (i) providing a heat exchanger that forms at least part of the first reboiler system;
      (ii) passing through the heat exchanger as a heating stream at least one stream selected from the group consisting of (I) the dehydrated product stream, (II) a reflux stream withdrawn from the second column, and (III) the second bottoms stream;
      (iii) passing a reboil stream withdrawn from the first column through the heat exchanger in heat exchanging relationship with the heating stream; and
   (f) recirculating the permeate stream within the process.

2. The process of claim 1, wherein the permeate stream is recirculated to the second distillation step.

3. The process of claim 1, wherein the permeate stream is recirculated to the first distillation step.

4. The process of claim 1, further comprising condensing the permeate stream before step (f).

5. The process of claim 1, wherein the membrane has a selectivity in favor of water over solvent of less than 100.

6. The process of claim 1, wherein the first distillation step further comprises a rectification step.

7. The process of claim 1, wherein step (b) is accomplished at least in part by heat exchange between the first portion of the mixture and the first overhead vapor stream.

8. The process of claim 4, wherein the permeate stream is condensed at least in part by heat exchange between the first portion of the mixture and the permeate stream.

9. The process of claim 1, further comprising passing a second portion of the mixture as a second feed stream into the second column.

10. The process of claim 1, further comprising recovering additional solvent from a second solvent and water mixture by passing at least a portion of the second solvent and water mixture as a second feed stream into the second column.

11. The process of claim 1, wherein the solvent comprises ethanol.

12. A process for recovering an organic solvent from a solvent and water mixture, comprising:
   (a) subjecting at least a first portion of the mixture to a first distillation step, carried out by passing a first feed stream of the mixture, at a first pressure, into a first column having a first reboiler system, to produce a solvent-enriched, first overhead vapor stream and a first bottoms stream, wherein the first bottoms stream consists essentially of water;
   (b) condensing the first overhead vapor stream to form a condensed overhead stream;

(c) pumping at least a portion of the condensed overhead stream to a second distillation step, carried out under a second pressure that is higher than the first pressure in a second column having a second reboiler system and a reflux condenser system, to produce a solvent-enriched, second overhead vapor stream and a second bottoms stream;

(d) performing a first membrane separation step, comprising:
  (i) providing a first membrane having a first feed side and a first permeate side, the membrane being selective in favor of water over solvent;
  (ii) passing at least a portion of the second overhead vapor stream at a first feed pressure across the first feed side;
  (iii) maintaining a first permeate pressure on the first permeate side that is lower than the first feed pressure;
  (iv) withdrawing a first residue stream from the first feed side;
  (v) withdrawing from the first permeate side a first permeate stream enriched in water compared with the second overhead vapor stream;

(e) performing a second membrane separation step, comprising:
  (i) providing a second membrane having a second feed side and a second permeate side, the membrane being selective in favor of water over solvent;
  (ii) passing at least a portion of the first residue stream at a second feed pressure across the second feed side;
  (iii) maintaining a second permeate pressure on the second permeate side that is lower than the second feed pressure;
  (iv) withdrawing from the second feed side, as a second residue stream, a dehydrated solvent product;
  (v) withdrawing from the second permeate side a second permeate stream enriched in water compared with the first residue stream;

(f) recovering heat by:
  (i) providing a heat exchanger that forms at least part of the first reboiler system;
  (ii) passing through the heat exchanger as a heating stream at least one stream selected from the group consisting of (I) the dehydrated product stream, (II) a reflux stream withdrawn from the second column, and (III) the second bottoms stream;
  (iii) passing a reboil stream withdrawn from the first column through the heat exchanger in heat exchanging relationship with the heating stream; and (g) recirculating the second permeate stream within the process.

13. The process of claim 12, wherein the second permeate pressure is lower than the first permeate pressure.

14. The process of claim 12, wherein the second permeate stream is recirculated to the second distillation step.

15. The process of claim 12, wherein the second permeate stream is recirculated to the first distillation step.

16. The process of claim 12, further comprising condensing the second permeate stream before step (g).

17. The process of claim 12, further comprising recirculating the first permeate stream within the process.

18. The process of claim 12, wherein step (b) is accomplished at least in part by heat exchange between the first portion of the mixture and the first overhead vapor stream.

19. The process of claim 16, wherein the second permeate stream is condensed at least in part by heat exchange between the first portion of the mixture and the second permeate stream.

20. The process of claim 12, wherein the both membranes have a selectivity in favor of water over solvent of less than 100.

21. The process of claim 12, wherein the first distillation step comprises a rectification step.

22. The process of claim 12, further comprising passing a second portion of the mixture as a second feed stream into the second column.

23. The process of claim 12, further comprising recovering additional solvent from a second solvent and water mixture by passing at least a portion of the second solvent and water mixture as a second feed stream into the second column.

24. The process of claim 12, wherein the solvent comprises ethanol.

25. A process for producing a light alcohol, comprising the following steps:
  (a) fermenting a sugar to form a fermentation broth comprising the alcohol and water;
  (b) subjecting the fermentation broth to a first distillation step, carried out by passing a first feed stream of at least a first portion of the fermentation broth, at a first pressure, into a first column having a first reboiler system, to produce an alcohol-enriched, first overhead vapor stream and a first bottoms stream, wherein the first bottoms stream consists essentially of water;
  (c) condensing the first overhead vapor stream to form a condensed overhead stream;
  (d) pumping at least a portion of the condensed overhead stream to a second distillation step, carried out under a second pressure that is higher than the first pressure in a second column having a second reboiler system and a reflux condenser system, to produce an alcohol-enriched, second overhead vapor stream and a second bottoms stream;
  (e) performing a membrane separation step, comprising:
    (i) providing a membrane having a feed side and a permeate side, the membrane being selective in favor of water over alcohol;
    (ii) passing at least a portion of the second overhead vapor stream at a feed pressure across the feed side;
    (iii) maintaining a permeate pressure on the permeate side that is lower than the feed pressure;
    (iv) withdrawing from the feed side, as a residue stream, a dehydrated alcohol product;
    (v) withdrawing from the permeate side a permeate stream enriched in water compared with the second overhead vapor stream;
  (f) recovering heat by:
    (i) providing a heat exchanger that forms at least part of the first reboiler system;
    (ii) passing through the heat exchanger as a heating stream at least one stream selected from the group consisting of (I) the dehydrated product stream, (II) a reflux stream withdrawn from the second column, and (III) the second bottoms stream;
    (iii) passing a reboil stream withdrawn from the first column through the heat exchanger in heat exchanging relationship with the heating stream; and
  (g) recirculating the permeate stream within the process.

26. The process of claim 25, wherein the sugar has been prepared by conversion of a plant biomass that comprises a starch or a cellulose.

27. The process of claim 25, wherein the alcohol comprises ethanol.

28. The process of claim 25, further comprising performing a filtration step between steps (a) and (b).

29. The process of claim 25, further comprising condensing the permeate stream before step (g), and wherein the permeate stream is recirculated as liquid to the fermentation step (a).

30. The process of claim 25, wherein step (c) is accomplished at least in part by heat exchange between the first portion of the fermentation broth and the first overhead vapor stream.

31. The process of claim 29, wherein the permeate stream is condensed at least in part by heat exchange between the first portion of the fermentation broth and the permeate stream.

32. The process of claim 25, further comprising passing a second portion of the fermentation broth as a second feed stream into the second column.

33. The process of claim 25, further comprising recovering additional alcohol from a second alcohol and water mixture by passing at least a portion of the second alcohol and water mixture as a second feed stream into the second column.

34. A process for producing a light alcohol, comprising the following steps:
(a) fermenting a sugar to form a fermentation broth comprising the alcohol and water;
(b) subjecting at least a first portion of the fermentation broth to a first distillation step, carried out by passing a first feed stream of the fermentation broth, at a first pressure, into a first column having a first reboiler system, to produce an alcohol-enriched, first overhead vapor stream and a first bottoms stream, wherein the first bottoms stream consists essentially of water;
(c) condensing the first overhead vapor stream to form a condensed overhead stream;
(d) pumping at least a portion of the condensed overhead stream to a second distillation step, carried out under a second pressure that is higher than the first pressure in a second column having a second reboiler system and a reflux condenser system, to produce an alcohol-enriched, second overhead vapor stream and a second bottoms stream;
(e) performing a first membrane separation step, comprising:
(i) providing a first membrane having a first feed side and a first permeate side, the membrane being selective in favor of water over alcohol;
(ii) passing at least a portion of the second overhead vapor stream at a first feed pressure across the first feed side;
(iii) maintaining a first permeate pressure on the first permeate side that is lower than the first feed pressure;
(iv) withdrawing a first residue stream from the first feed side;
(v) withdrawing from the first permeate side a first permeate stream enriched in water compared with the second overhead vapor stream;
(f) performing a second membrane separation step, comprising:
(i) providing a second membrane having a second feed side and a second permeate side, the membrane being selective in favor of water over alcohol;
(ii) passing at least a portion of the first residue stream at a second feed pressure across the second feed side;
(iii) maintaining a second permeate pressure on the second permeate side that is lower than the second feed pressure;
(iv) withdrawing from the second feed side, as a second residue stream, a dehydrated alcohol product;
(v) withdrawing from the second permeate side a second permeate stream enriched in water compared with the first residue stream;
(g) recovering heat by:
(i) providing a heat exchanger that forms at least part of the first reboiler system;
(ii) passing through the heat exchanger as a heating stream at least one stream selected from the group consisting of (I) the dehydrated product stream, (II) a reflux stream withdrawn from the second column, and (III) the second bottoms stream;
(iii) passing a reboil stream withdrawn from the first column through the heat exchanger in heat exchanging relationship with the heating stream; and
(h) recirculating the second permeate stream within the process.

35. The process of claim 34, wherein the second permeate pressure is lower than the first permeate pressure.

36. The process of claim 34, wherein the sugar has been prepared by conversion of a plant biomass that comprises a starch or a cellulose.

37. The process of claim 34, wherein the alcohol comprises ethanol.

38. The process of claim 34, further comprising performing a filtration step between steps (a) and (b).

39. The process of claim 34, further comprising condensing the second permeate stream before step (h), and wherein the second permeate stream is recirculated as liquid to the fermentation step (a).

40. The process of claim 34, further comprising recirculating the first permeate stream within the process.

41. The process of claim 34, wherein step (c) is accomplished at least in part by heat exchange between the first portion of the fermentation broth and the first overhead vapor stream.

42. The process of claim 39, wherein the second permeate stream is condensed at least in part by heat exchange between the first portion of the fermentation broth and the second permeate stream.

43. The process of claim 34, further comprising passing a second portion of the fermentation broth as a second feed stream into the second column.

44. The process of claim 34, further comprising recovering additional alcohol from a second alcohol and water mixture by passing at least a portion of the second alcohol and water mixture as a second feed stream into the second column.

45. A process for recovering an organic solvent from a solvent and water mixture, comprising:
(a) subjecting a first portion of the mixture to a first distillation step at a first pressure, carried out by passing a first feed stream of the mixture into a first column having a first reboiler system, to produce a solvent-enriched, first overhead vapor stream and a first bottoms stream, wherein the first bottoms stream consists essentially of water;
(b) condensing the first overhead vapor stream to form a condensed overhead stream;
(c) passing a second portion of the mixture and pumping at least a portion of the condensed overhead stream to a second distillation step carried out under a second pressure that is higher than the first pressure in a second column having a second reboiler system and a reflux condenser system, to produce a solvent-enriched, second overhead vapor stream and a second bottoms stream;

(d) performing a membrane separation step, comprising:
  (i) providing a membrane having a feed side and a permeate side, the membrane being selective in favor of water over solvent;
  (ii) passing at least a portion of the second overhead vapor stream at a feed pressure across the feed side;
  (iii) maintaining a permeate pressure on the permeate side that is lower than the feed pressure;
  (iv) withdrawing from the feed side, as a residue stream, a dehydrated product stream;
  (v) withdrawing from the permeate side a permeate stream enriched in water compared with the second overhead vapor stream;

(e) recovering heat by:
  (i) providing a heat exchanger that forms at least part of the first reboiler system;
  (ii) passing through the heat exchanger as a heating stream at least one stream selected from the group consisting of (I) the dehydrated product stream, (II) a reflux stream withdrawn from the second column, and (III) the second bottoms stream;
  (iii) passing a reboil stream withdrawn from the first column through the heat exchanger in heat exchanging relationship with the heating stream; and (f) recirculating the first permeate stream within the process.

46. The process of claim 45, wherein the permeate stream is recirculated to the second distillation step.

47. The process of claim 45, wherein the permeate stream is recirculated to the first distillation step.

48. The process of claim 45, further comprising condensing the permeate stream before step (f).

49. The process of claim 45, wherein the first distillation step further comprises a rectification step.

50. The process of claim 45, wherein step (b) is accomplished at least in part by heat exchange between the first portion of the mixture and the first overhead vapor stream.

51. The process of claim 48, wherein the permeate stream is condensed at least in part by heat exchange between the first portion of the mixture and the permeate stream.

52. The process of claim 45, wherein the solvent comprises ethanol.

53. A process for recovering an organic solvent from a solvent and water mixture, comprising:

(a) subjecting at least a first portion of the mixture to a first distillation step, carried out by passing a first feed stream of the mixture, at a first pressure, into a first column having a first reboiler system, to produce a solvent-enriched, first overhead vapor stream and a first bottoms stream, wherein the first bottoms stream consists essentially of water;

(b) condensing the first overhead vapor stream to form a condensed overhead stream;

(c) passing a second portion of the mixture and pumping at least a portion of the condensed overhead stream to a second distillation step, carried out under a second pressure that is higher than the first pressure in a second column having a second reboiler system and a reflux condenser system, to produce a solvent-enriched, second overhead vapor stream and a second bottoms stream;

(d) performing a first membrane separation step, comprising:
  (i) providing a first membrane having a first feed side and a first permeate side, the membrane being selective in favor of water over solvent;
  (ii) passing at least a portion of the second overhead vapor stream at a first feed pressure across the first feed side;
  (iii) maintaining a first permeate pressure on the first permeate side that is lower than the first feed pressure;
  (iv) withdrawing a first residue stream from the first feed side;
  (v) withdrawing from the first permeate side a first permeate stream enriched in water compared with the second overhead vapor stream;

(e) performing a second membrane separation step, comprising:
  (i) providing a second membrane having a second feed side and a second permeate side, the membrane being selective in favor of water over solvent;
  (ii) passing at least a portion of the first residue stream at a second feed pressure across the second feed side;
  (iii) maintaining a second permeate pressure on the second permeate side that is lower than the second feed pressure;
  (iv) withdrawing from the second feed side, as a second residue stream, a dehydrated solvent product;
  (v) withdrawing from the second permeate side a second permeate stream enriched in water compared with the first residue stream;

(f) recovering heat by:
  providing a heat exchanger that forms at least part of the first reboiler system;
  (ii) passing through the heat exchanger as a heating stream at least one stream selected from the group consisting of (I) the dehydrated product stream, (II) a reflux stream withdrawn from the second column, and (III) the second bottoms stream;
  (iii) passing a reboil stream withdrawn from the first column through the heat exchanger in heat exchanging relationship with the heating stream; and (g) recirculating the second permeate stream within the process.

54. The process of claim 53, wherein the second permeate pressure is lower than the first permeate pressure.

55. The process of claim 53, wherein the second permeate stream is recirculated to the second distillation step.

56. The process of claim 53, wherein the second permeate stream is recirculated to the first distillation step.

57. The process of claim 53, further comprising condensing the second permeate stream before step (g).

58. The process of claim 53, further comprising recirculating the first permeate stream within the process.

59. The process of claim 53, wherein the first distillation step comprises a rectification step.

60. The process of claim 53, wherein step (b) is accomplished at least in part by heat exchange between the first portion of the mixture and the first overhead vapor stream.

61. The process of claim 57, wherein the second permeate stream is condensed at least in part by heat exchange between the second portion of the mixture and the first permeate stream.

62. The process of claim 53, wherein the solvent comprises ethanol.

\* \* \* \* \*